United States Patent
George

(10) Patent No.: US 11,653,919 B2
(45) Date of Patent: May 23, 2023

(54) STAPLER LINE REINFORCEMENT CONTINUITY

(71) Applicant: Covidien LP, Mansfield, MA (US)

(72) Inventor: Sabastian K. George, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/102,629

(22) Filed: Nov. 24, 2020

(65) Prior Publication Data

US 2022/0160356 A1    May 26, 2022

(51) Int. Cl.
*A61B 17/072* (2006.01)
*A61B 17/00* (2006.01)

(52) U.S. Cl.
CPC .......... *A61B 17/07207* (2013.01); *A61B 2017/00477* (2013.01); *A61B 2017/00818* (2013.01); *A61B 2017/07257* (2013.01); *A61B 2017/07271* (2013.01); *A61B 2017/07285* (2013.01)

(58) Field of Classification Search
CPC .............. A61B 17/068; A61B 17/0684; A61B 17/0686; A61B 17/07292; A61B 17/07207; A61B 2017/07271; A61B 2017/00818; A61B 2017/07257; A61B 2017/00477; A61B 2017/07285
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).

(Continued)

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

An end effector of a surgical stapling apparatus includes an anvil assembly and a cartridge assembly. The anvil assembly has an anvil body that supports an anvil buttress. The anvil buttress includes a distal alignment band that extends distally beyond the anvil body. The cartridge assembly has a cartridge body that supports a cartridge buttress. The cartridge buttress includes a distal alignment band that extends distally beyond the cartridge body.

20 Claims, 7 Drawing Sheets

(56) References Cited

U.S. PATENT DOCUMENTS

| | | |
|---|---|---|
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Foung et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |

(56) References Cited

U.S. PATENT DOCUMENTS

| | | |
|---|---|---|
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,099,551 A * | 8/2000 | Gabbay ............ A61B 17/07207 227/176.1 |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |

(56) References Cited

U.S. PATENT DOCUMENTS

| | | | |
|---|---|---|---|
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0147922 A1* | 6/2010 | Olson ............... A61B 17/105 227/176.1 |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0215132 A1 | 9/2011 | Aranyi et al. |
| 2011/0301579 A1 | 12/2011 | Marczyk et al. |
| 2011/0303735 A1 | 12/2011 | Marczyk |

(56) References Cited

U.S. PATENT DOCUMENTS

| | | | |
|---|---|---|---|
| 2012/0055972 A1 | 3/2012 | Marczyk | |
| 2012/0074197 A1 | 3/2012 | Marczyk | |
| 2012/0175400 A1 | 7/2012 | Viola et al. | |
| 2012/0193393 A1 | 8/2012 | Viola et al. | |
| 2012/0198288 A1 | 8/2012 | Njo et al. | |
| 2012/0220989 A1 | 8/2012 | Zemlok et al. | |
| 2012/0223121 A1 | 9/2012 | Viola et al. | |
| 2012/0241494 A1 | 9/2012 | Marczyk | |
| 2012/0277790 A1 | 11/2012 | Zemlok et al. | |
| 2012/0298718 A1 | 11/2012 | Marczyk | |
| 2012/0298720 A1 | 11/2012 | Marczyk | |
| 2015/0305743 A1* | 10/2015 | Casasanta | A61B 17/105 227/176.1 |
| 2015/0351758 A1* | 12/2015 | Shelton, IV | A61B 17/0644 606/219 |
| 2018/0125491 A1* | 5/2018 | Aranyi | A61B 17/07207 |

FOREIGN PATENT DOCUMENTS

| | | | | |
|---|---|---|---|---|
| EP | 0537570 | A2 | 4/1993 | |
| EP | 0647431 | A2 | 4/1995 | |
| EP | 0738501 | A1 | 10/1996 | |
| EP | 0770354 | A1 | 5/1997 | |
| EP | 1070487 | A2 | 1/2001 | |
| EP | 1201196 | A1 | 5/2002 | |
| EP | 1658817 | A1 | 5/2006 | |
| EP | 1813203 | A2 | 8/2007 | |
| EP | 2311386 | A2 | 4/2011 | |
| EP | 3162301 | A2 * | 5/2017 | A61B 17/068 |
| EP | 3566658 | A2 * | 11/2019 | A61B 17/07292 |
| FR | 2736817 | A1 * | 1/1997 | A61B 17/07207 |
| FR | 2 849 589 | A1 | 7/2004 | |
| WO | 9414129 | A1 | 6/1994 | |
| WO | 9729694 | A1 | 8/1997 | |
| WO | 9740760 | A1 | 11/1997 | |
| WO | 9837825 | A1 | 9/1998 | |
| WO | 1999/52489 | A1 | 10/1999 | |
| WO | 0234140 | A2 | 5/2002 | |
| WO | 03026511 | A1 | 4/2003 | |
| WO | 03030743 | A2 | 4/2003 | |
| WO | 2004032760 | A2 | 4/2004 | |
| WO | 2007030753 | A2 | 3/2007 | |
| WO | 2007/114868 | A2 | 10/2007 | |
| WO | 2007118179 | A2 | 10/2007 | |
| WO | 2007014355 | A3 | 4/2009 | |
| WO | 2009143092 | A1 | 11/2009 | |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15—1-Sire SHA-256 Secure Authenticator with 512-Bit User EEPROM"; IC-On-Line, Electronic Component Manufacturers, pp. 1-2; Aug. 2013.

Extended European Search Report for Application No. 21210080.4 dated Apr. 11, 2022.

\* cited by examiner

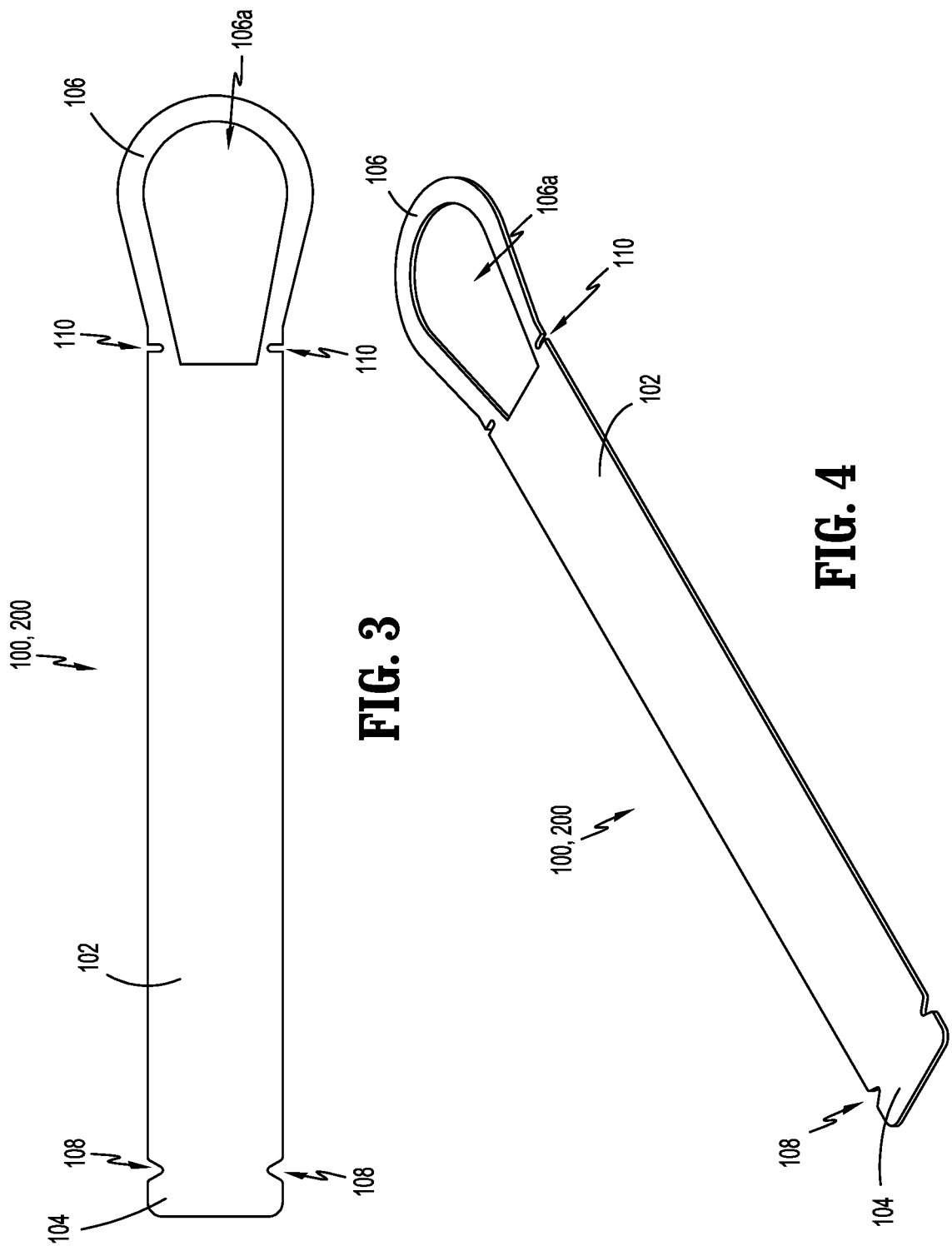

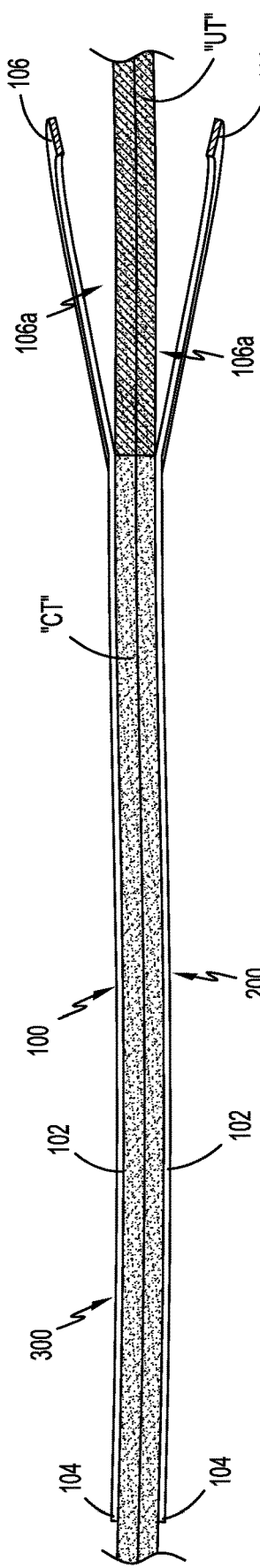
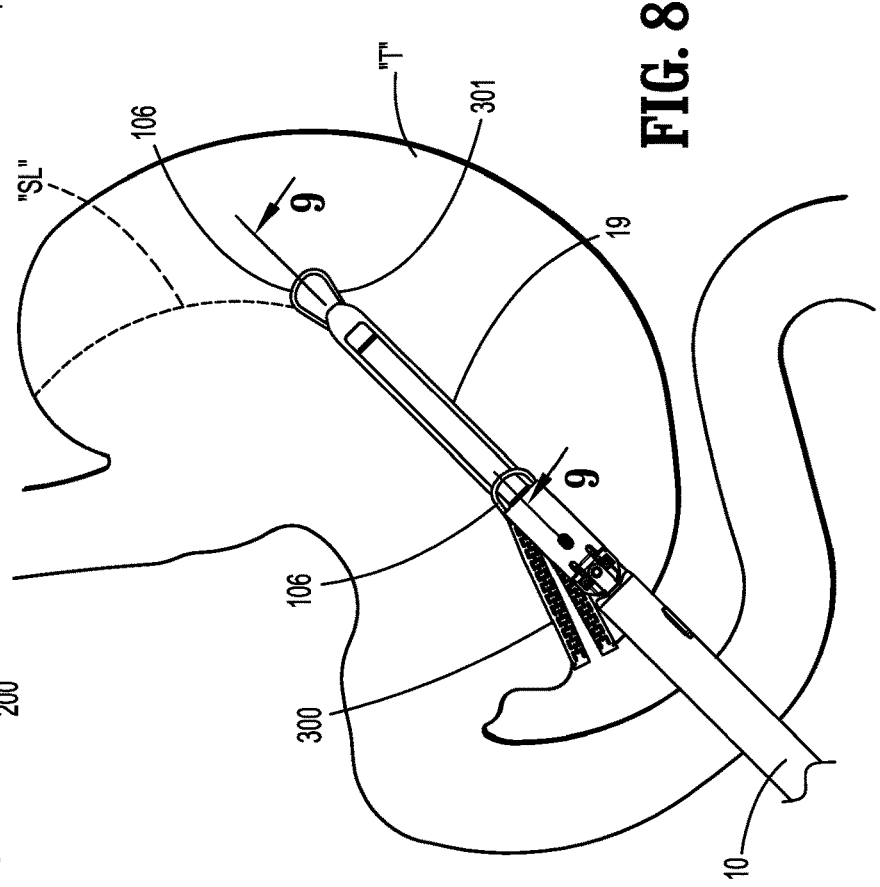
FIG. 7
FIG. 8

STAPLER LINE REINFORCEMENT CONTINUITY

TECHNICAL FIELD

This application relates to surgical stapling systems and more particularly, to systems, devices, and methods for applying buttressed staple lines with surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired," staple drive members in one of the jaws push the surgical staples through the body tissue and into an anvil in the opposite jaw which forms the staples. If body tissue is to be removed or separated, a knife blade can be provided in one of the jaws of the apparatus to cut the body tissue between the lines of staples.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple line as well as covers the juncture of the tissues to reduce leakage prior to healing. The buttress material can help promote proper staple formation while reducing twisting/malformation caused by any misalignment of tissue and/or unusual or non-uniform tissue. The buttress material can also provide support to weakened tissue, or help address differences in the thickness of tissues.

Accordingly, buttress materials provide clinical benefits. Nonetheless, improvements are desired, for example, to reduce the complexity of manufacture and/or application of the buttress materials onto surgical stapling apparatus or into tissue, or to expand the range of application for use of the buttress materials.

SUMMARY

According to one aspect of this disclosure, an end effector of a surgical stapling apparatus includes an anvil assembly and a cartridge assembly. The anvil assembly has an anvil body that supports an anvil buttress. The anvil buttress includes a distal alignment band that extends distally beyond the anvil body. The cartridge assembly has a cartridge body that supports a cartridge buttress. The cartridge buttress includes a distal alignment band that extends distally beyond the cartridge body.

In aspects of this disclosure, the anvil buttress may be secured to the anvil body by one or more sutures. The one or more sutures may include a proximal suture. The anvil buttress may include proximal suture recesses that receive the proximal suture to facilitate securement of a proximal portion of the anvil buttress to the anvil body. The one or more sutures may include a distal suture. The anvil buttress may include distal suture recesses that receive the distal suture to facilitate securement of a distal portion of the anvil buttress to the anvil body. The proximal suture recesses may define a proximal tail.

In aspects of this disclosure, the cartridge buttress may be secured to the anvil body by one or more sutures. The one or more sutures may include a proximal suture. The cartridge buttress may include proximal suture recesses that receive the proximal suture to facilitate securement of a proximal portion of the cartridge buttress to the cartridge body. The one or more sutures may include a distal suture. The cartridge buttress may include distal suture recesses that receive the distal suture to facilitate securement of a distal portion of the cartridge buttress to the cartridge body.

In aspects of this disclosure, the cartridge body may support a removable staple cartridge.

According to one aspect of this disclosure, a surgical stapling apparatus includes an elongated tubular body portion and an end effector supported on elongated tubular body portion. The end effector includes an anvil assembly and a cartridge assembly. The anvil assembly has an anvil body that supports an anvil buttress. The anvil buttress includes a distal alignment band that extends distally beyond the anvil body. The cartridge assembly has a cartridge body that supports a cartridge buttress. The cartridge buttress includes a distal alignment band that extends distally beyond the cartridge body.

BRIEF DESCRIPTION OF THE DRAWINGS

The above and other aspects, features, and advantages of this disclosure will be apparent in light of the following detailed description when taken in conjunction with the accompanying drawings, which are incorporated in and constitute a part of this specification, wherein:

FIG. 3 is an enlarged, top view of a buttress of the surgical stapling apparatus of FIG. 1;

FIG. 4 is a perspective view of the buttress of FIG. 3;

FIG. 7 is an enlarged, cross-sectional view as taken along section line 7-7 of FIG. 6;

FIG. 8 is a top view illustrating the surgical stapling apparatus of FIG. 1 attaching a second buttress assembly to the stomach at a position along the stomach adjacent to the first buttress assembly;

DETAILED DESCRIPTION

Figure 1:
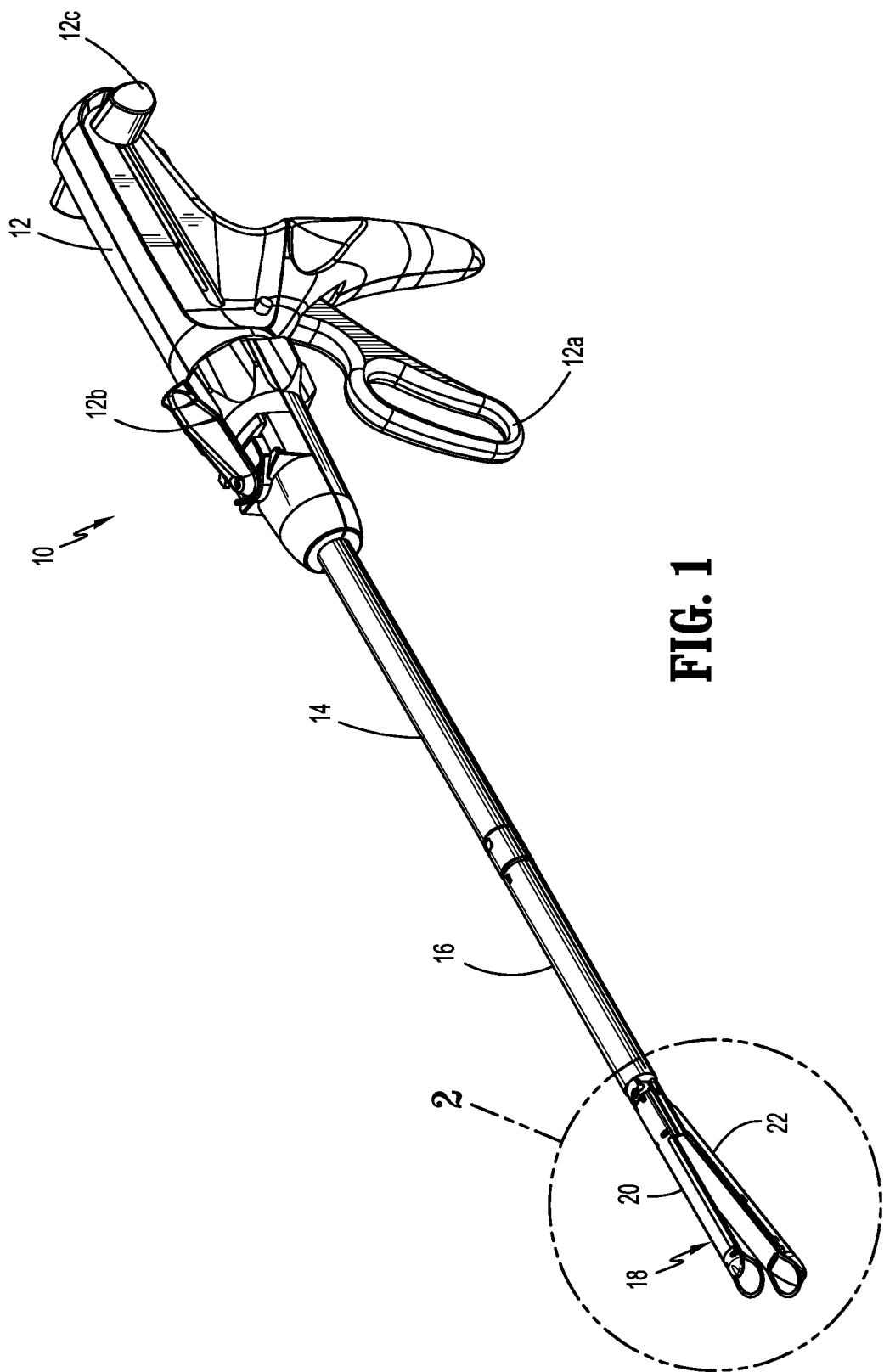
FIG. 1 is a perspective view of a surgical stapling apparatus in accordance with the principles of this disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the aspects and are not intended to have any limiting effect on the ultimate orientation of a structure or any part thereof. In the following description, well-known functions or constructions are not described in detail to avoid obscuring this disclosure in unnecessary detail.

During sleeve gastrectomy, it is essential to use multiple cartridges to cut and staple the stomach. When these cartridge are used back to back, their sequence of alignment, one over the other, is not perfect. Sometimes, a second firing starts behind the end of a first firing and sometimes the second or third firing are disposed at an angle relative to the first or the second firing. In order to achieve continuity of stapler lines during a firing cycle, this disclosure details surgical stapling apparatus including end effectors with buttresses having distal alignment bands that help to prevent overfiring on a prior firing and facilitate alignment with the prior firing.

Referring now to FIGS. 1-10, a surgical stapling system, in accordance with this disclosure, includes a surgical stapling apparatus or surgical stapler 10. The surgical stapling apparatus 10 generally includes a handle assembly 12 and an elongated tubular body portion 14 that extends distally from the handle assembly 12, which may be in the form of an adapter assembly selectively removable from handle assembly 12. The elongated tubular body portion 14 may include a surgical loading unit 16 that is selectively attachable to the elongated tubular body portion 14. An end effector or jaw assembly 18 extends distally from the elongated tubular body portion 14 (e.g., a distal end portion of the surgical loading unit 16). The jaw assembly 18 includes an anvil assembly 20 and a staple cartridge assembly 22. The jaw assembly 18 may be permanently affixed to the elongated tubular body portion 14 or may be detachable with respect to the elongated tubular body portion 14 and thus, replaceable with a new jaw assembly 18. The anvil assembly 20 and/or the staple cartridge assembly 22 is pivotable with respect to the elongated tubular body portion 14 such that the anvil and/or staple cartridge assemblies 20, 22 is/are movable between an open position in which the anvil and staple cartridge assemblies 20, 22 are spaced apart with respect to each other (FIGS. 1 and 2) and a closed position (not shown) in which the anvil and staple cartridge assemblies 20, 22 are substantially adjacent each other.

The handle assembly 12 of the surgical stapling apparatus 10 includes any number of actuators 12a, 12b, 12c to facilitate a firing of jaw assembly 18, an articulation and/or rotation of the jaw assembly 18 relative to handle assembly 12, and/or an opening and/or closing of anvil and/or cartridge assemblies 20, 22 to clamp tissue therebetween. Jaw assembly 18 is configured to apply lines of staples (not shown) to tissue captured between the anvil and staple cartridge assemblies 20, 22 when fired.

For a detailed description of the structure and function of exemplary surgical stapling apparatus, one or more components of which may be included, or modified for use with the disclosed aspects, reference may be made to U.S. Pat. Nos. 8,256,656, 7,819,896, and 7,128,253 as well as U.S. patent application Ser. No. 16/387,882, filed Apr. 18, 2019, the entire contents of each of which is incorporated herein by reference. It should be appreciated that principles of this disclosure are equally applicable to surgical stapling apparatus having other configurations such as, for example, the types described in U.S. Pat. Nos. 7,334,717, 5,964,394, and 5,915,616, the entire contents of each of which is incorporated herein by reference. Accordingly, it should be understood that a variety of surgical stapling apparatus may be utilized with the surgical buttresses and/or surgical buttress applicators or loaders of this disclosure such as, for example, laparoscopic staplers, open staplers, transverse anastomosis staplers, and end-to-end anastomosis staplers having a circular staple cartridge and anvil, as well as staple cartridge assemblies housing surgical fasteners other than staples.

Figure 2:
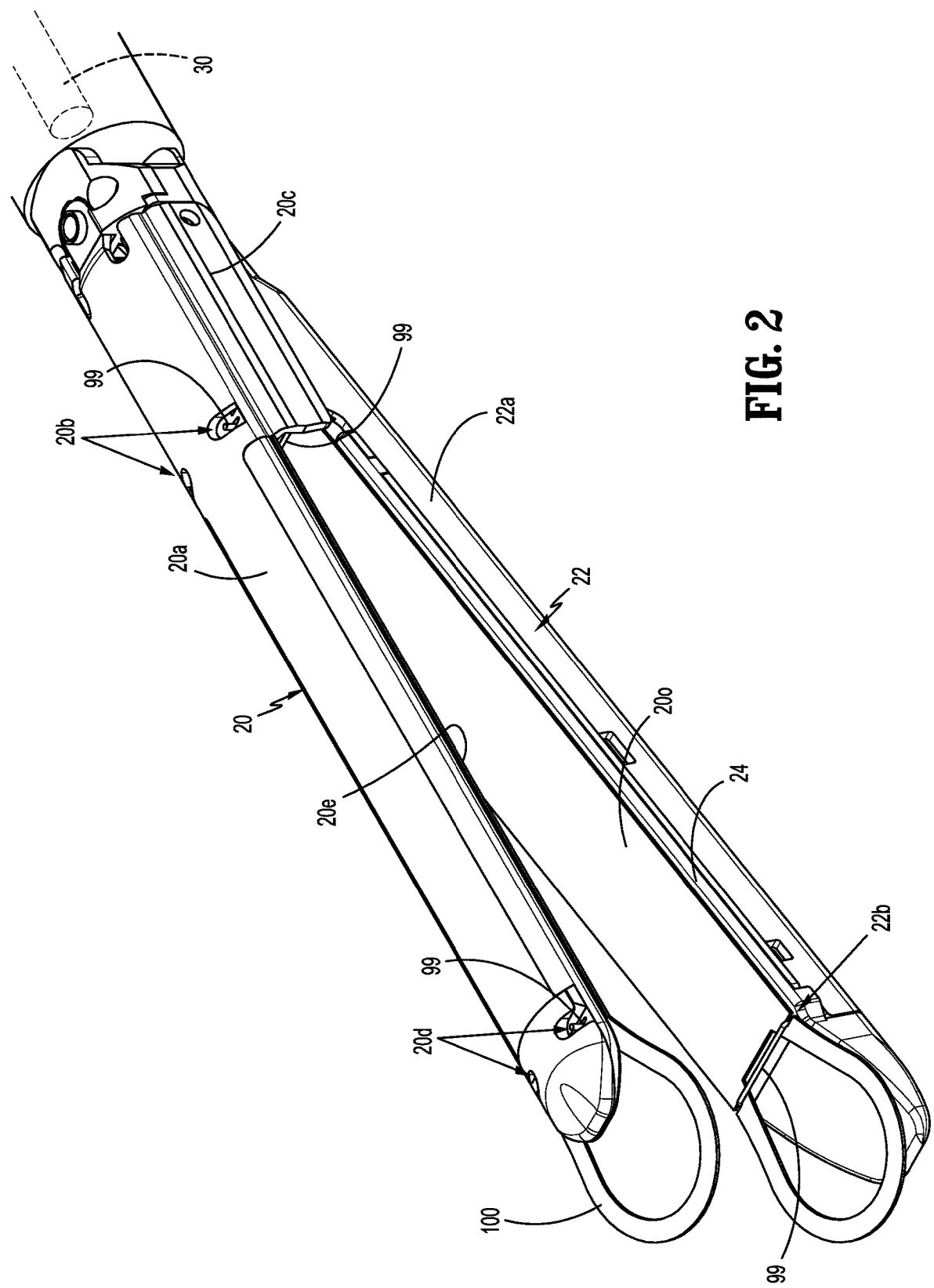
FIG. 2 is an enlarged view of the indicated area of detail shown in FIG. 1.

As seen in FIG. 2, anvil assembly 20 of jaw assembly 18 of surgical stapling apparatus 10 supports an anvil buttress 100 and includes an anvil body 20a. Anvil body 20a has a proximal end portion defining proximal suture slots 20b and includes a tissue stop 20c configured to prevent proximal tissue migration. Anvil body 20a extends to distal end portion defining distal suture slots 20d. Proximal and distal suture slots 20b, 20d receive sutures 99 therethrough that secure anvil buttress 100 to anvil body 20a so that anvil buttress 100 abuts and covers a plurality of rows of staple forming pockets (not shown) of an anvil 20e of anvil body 20a.

Similarly, cartridge assembly 22 of jaw assembly 18 supports a cartridge buttress 200 and includes a cartridge body 22a. Cartridge body 22a supports a staple cartridge 24 that houses a plurality of rows of staples 26 (FIG. 6) in staple retaining slots defined therein (not shown). Cartridge body 22a has a proximal end portion defining proximal and distal suture slots 22b that receive sutures 99 therethrough for securing cartridge buttress 200 to cartridge body 22a so that cartridge buttress 200 abuts and covers the staple retaining slots of staple cartridge 24.

With reference to FIGS. 3 and 4, buttresses 100, 200 include a buttress body 102 having a proximal tail 104 and a distal alignment band 106. Distal alignment band 106 circumscribes an elongated distal opening 106a. Buttress body 102 defines proximal suture recesses 108 on opposite sides thereof adjacent proximal tail 104 and distal suture recesses 110 within a proximal end portion of distal alignment band 106. When buttress bodies 102 of anvil and cartridge buttresses 100, 200 are secured to end effector 18 via sutures 99 (see FIG. 2), distal alignment bands 106 of anvil and cartridge buttresses 100, 200 extend distally beyond and free from anvil and cartridge bodies 20a, 22a of anvil and cartridge assemblies 20, 22 so that elongated distal openings 106a thereof (e.g., a majority thereof) extend distally beyond distal ends of anvil and cartridge bodies 20a, 22a.

Figure 5:
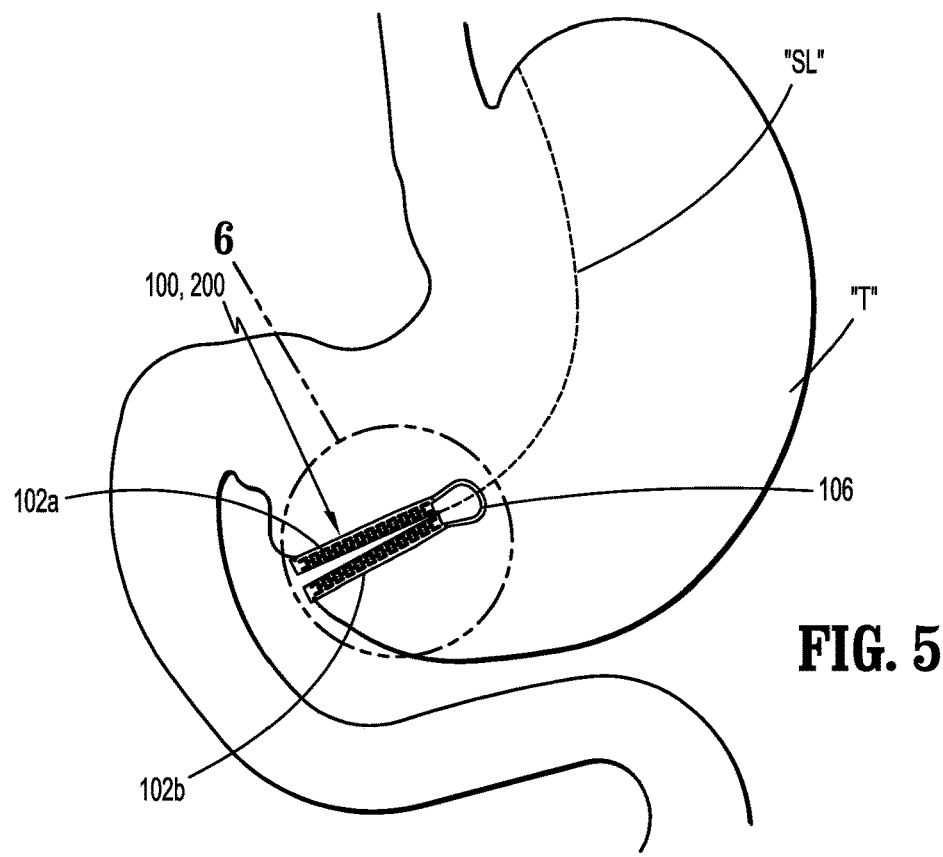
FIG. 5 is a top view illustrating a first buttress system of the surgical stapling apparatus shown secured to a stomach.
Figure 6:
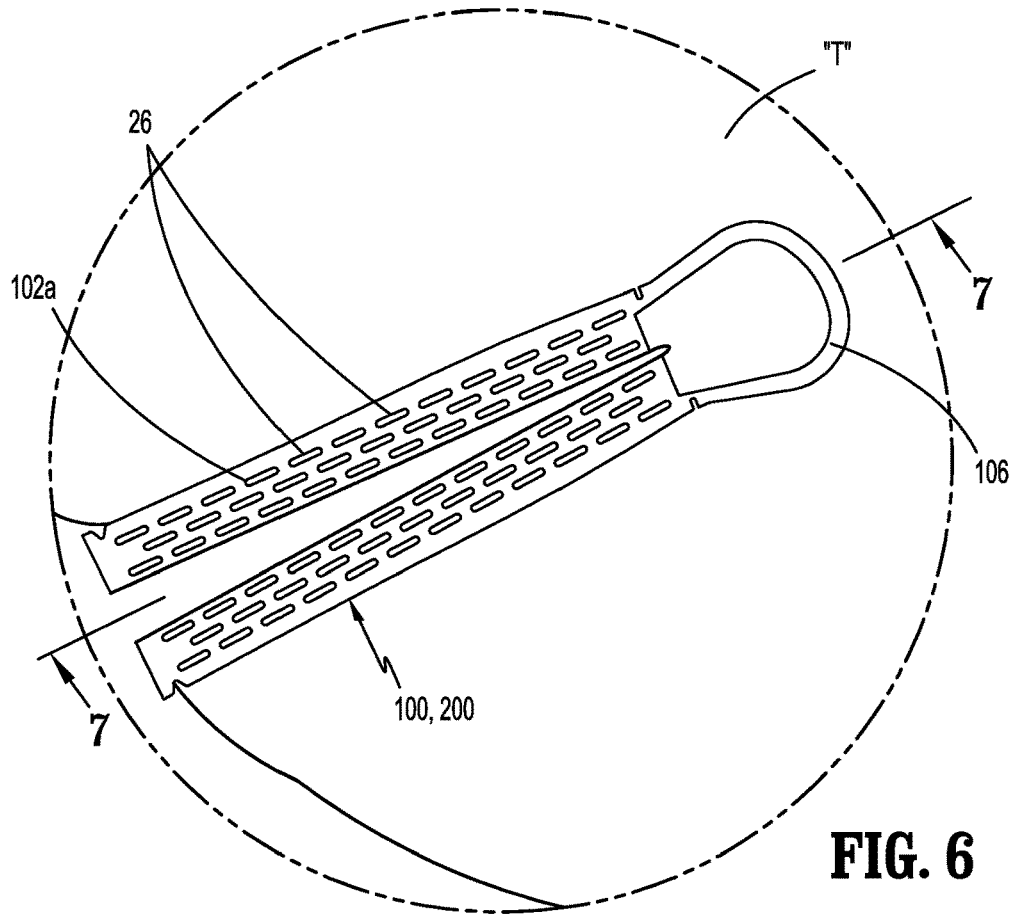
FIG. 6 is an enlarged view of the indicated area of detail shown in FIG. 5.

Turning now to FIGS. 5-7, surgical stapler 10 is fired at a first location along a surgical line "SL" of tissue "T" (e.g., stomach tissue in a sleeve gastrectomy procedure) so that buttress bodies 102 of anvil and cartridge buttresses 100, 200 are secured along the staple line "SL" on opposite sides of the tissue "T" and form a first buttress assembly 300. A knife assembly 30 (see FIG. 2) of surgical stapler 10 cuts through sutures 99 and buttress bodies 102 of anvil and cartridge buttresses 100, 200 without cutting through distal alignment bands 106 thereof so that buttress bodies 102 separate from respective anvil and cartridge assemblies 20, 22. Each buttress body 102 is divided by knife assembly 30 into two elongate sections 102a, 102b connected together by opposite ends of distal alignment bands 106. Bands 106 extend over uncut tissue "UT" and distally beyond cut tissue "CT" along surgical line "SL."

Figure 9:
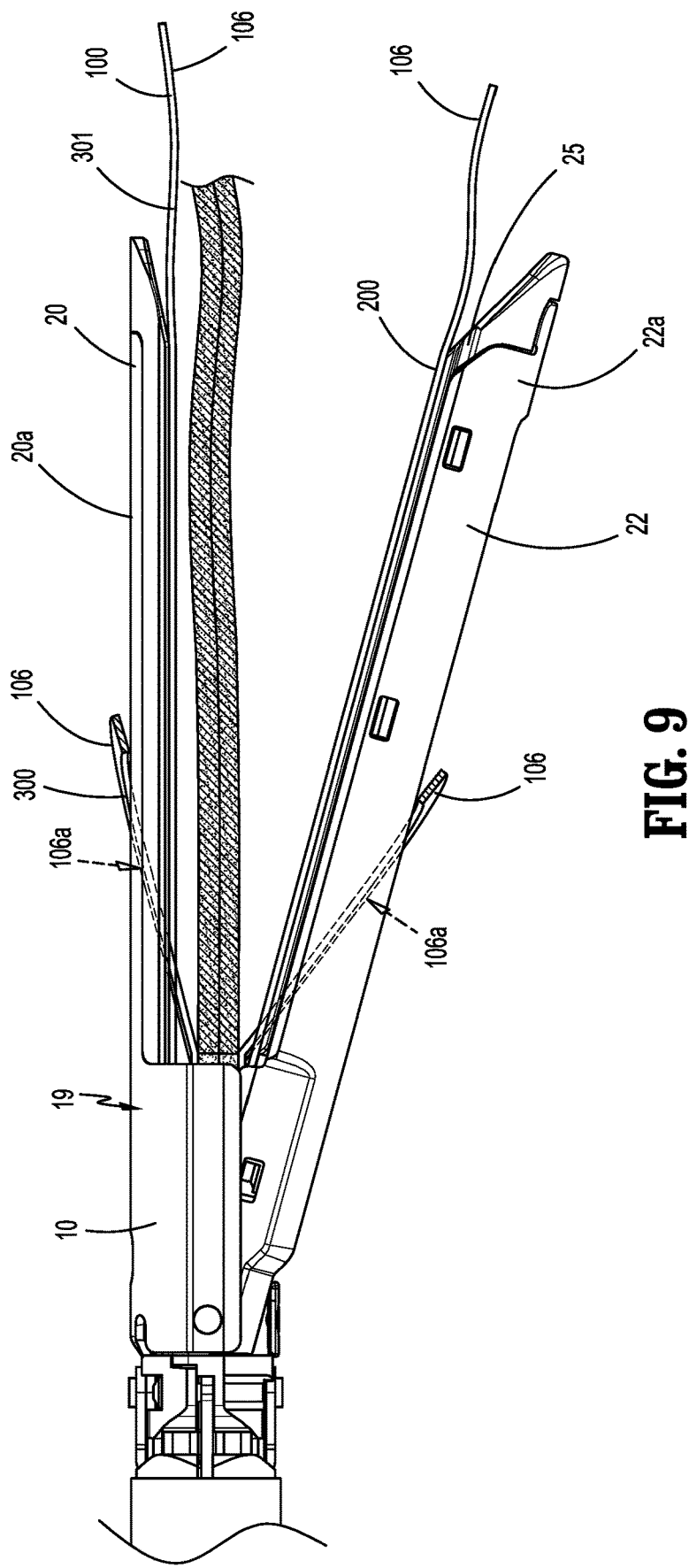
FIG. 9 is an enlarged, cross-sectional view as taken along section line 9-9 of FIG. 8.
Figure 10:
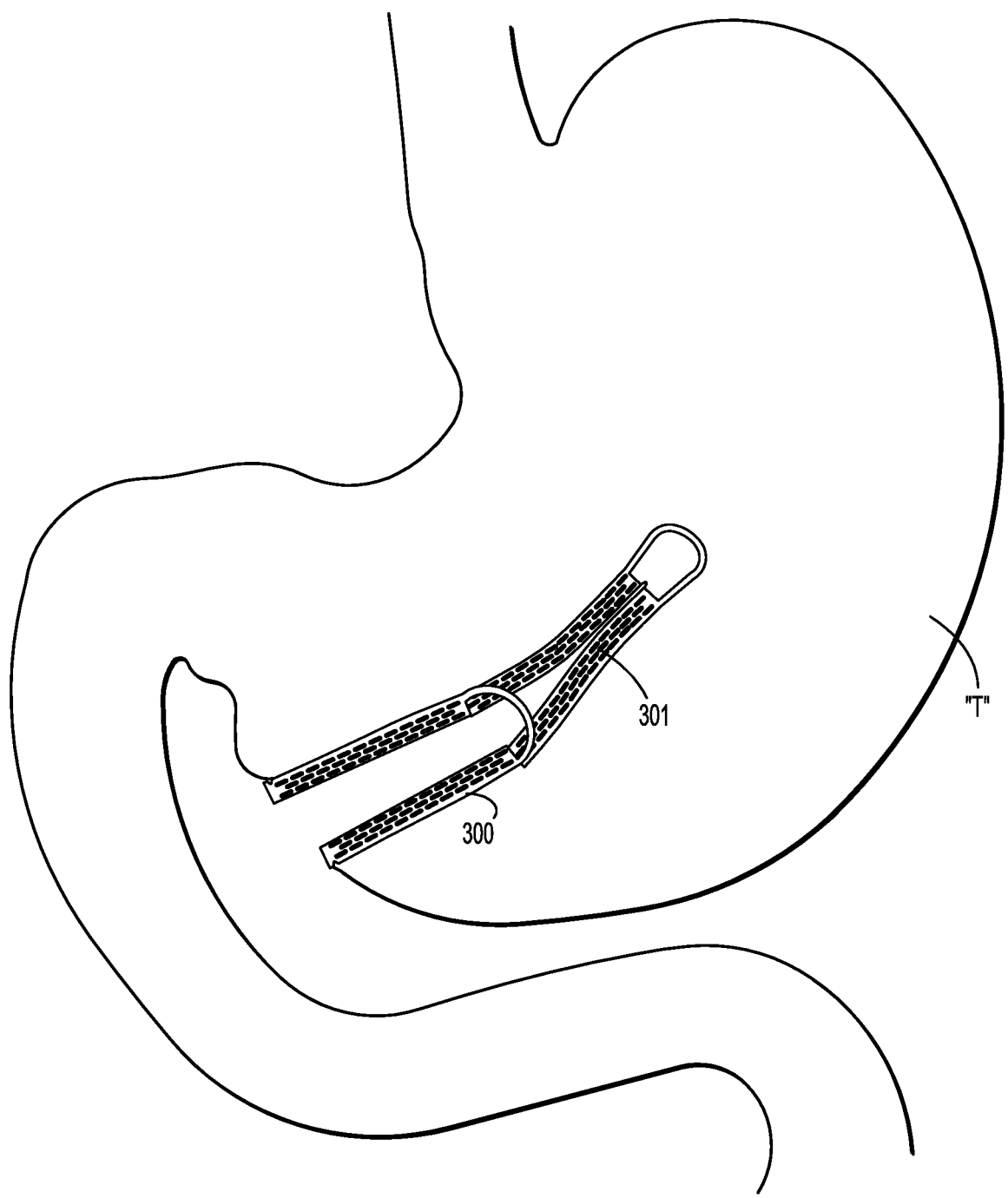
FIG. 10 is a perspective view of the stomach with the first and second buttress assemblies attached thereto before distal alignment bands of the first and second buttress assemblies are cut.

With reference to FIGS. 8-10, with first buttress assembly 300 secured along surgical line "SL" at a first location, surgical stapler 10 is reloaded with a second staple cartridge 25 and a second buttress assembly 301 to define a reloaded end effector 19. Second buttress assembly 301 includes another anvil buttress 100 and another cartridge buttress 200. Reloaded end effector 19 is then inserted through distal openings 106a of anvil and cartridge buttresses 100, 200 such that anvil assembly 20 extends through distal opening 106a of anvil buttress 100 and cartridge assembly 22 extends through distal opening 106a of cartridge buttress 200 to secure second buttress assembly 301 at a second location along surgical line "SL." Surgical stapler 10 is then reloaded and the process is continuously repeated along the length of surgical line "SL." Once all surgical buttress assemblies are secured along the length of the surgical line "SL," distal alignment bands 106 of all of the respective anvil and cartridge buttresses 100, 200 can then be cut by, for example, a separate cutter (not shown) to enable a portion of the tissue "T" (e.g., stomach tissue) to be separated from the remainder of the tissue "T."

The surgical buttresses 100, 200 of this disclosure may be fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttresses. The surgical buttresses may be biodegradable (e.g., formed from bioabsorbable and bioresorable materials) such that the surgical buttresses decompose or are broken down (physically or chemically) under physiological conditions in the body, and the degradation products are excretable or absorbable by the body. Components or portions of the surgical buttresses may be formed from the same material or different materials.

In aspects, at least a portion of the surgical buttresses are made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In aspects, at least a portion of the surgical buttresses may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The surgical buttresses may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses, or portions thereof, may be a non-woven structure formed by melt-blown or melt-spun methods, a mesh material, a braid material, and/or a molded or extruded sheet. The surgical buttresses, or portions thereof, may be a single porous or non-porous layer, or include a plurality of layers including any combination of porous and/or non-porous layers.

The surgical buttresses may be provided and/or sold as part of the buttress loader and/or loading unit. Alternatively, the surgical buttress(es), the buttress loader, and/or the loading units may be provided and/or sold separately and assembled by the user. In aspects, one or more surgical buttresses, one or more buttress loaders, and/or loading units are provided in a kit. In some aspects, the kit further includes one or more end effectors (and/or surgical loading units) and, in certain aspects, the kit further includes a surgical stapler.

In any of the aspects disclosed herein, the surgical buttresses can include, or be used with, brachytherapy, chemotherapy, other medical materials or pharmaceuticals. The buttress portion of the surgical buttress can have pockets, apertures, or other features for retaining brachytherapy seeds with the buttress portion, or brachytherapy seeds or materials can be incorporated into a suture or sutures that are threaded into or through the buttress portion or otherwise attached thereto. A coating having brachytherapy materials can be applied to a buttress portion of a surgical buttress by spraying or dipping. Chemotherapy pharmaceuticals or agents can be incorporated into the buttress portion of the surgical buttress, coated thereon, or otherwise applied as part of a suture or other feature secured to the buttress portion.

As can be appreciated, securement of any of the components of the presently disclosed apparatus can be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, it is envisioned that the elements and features illustrated or described in connection with one exemplary aspect may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. An end effector of a surgical stapling apparatus, the end effector comprising:
   an anvil assembly having an anvil body that supports an anvil buttress, the anvil buttress includes a first distal alignment band having a proximal portion with first and second ends secured to an anvil buttress body of the anvil buttress so that a remainder of the first distal alignment band is unattached from the end effector, the first distal alignment band circumscribing a first elongated distal opening having a first length and separating the first and second ends, wherein a distal portion of the anvil buttress body is secured to a distal portion of the anvil body with a first structure so that at least a majority of the first length of the first elongated distal opening of the first distal alignment band extends distally beyond a remainder of the anvil assembly, the first elongated distal opening configured to simultaneously receive the anvil body and a second anvil buttress attached to the anvil body through the first elongated distal opening when the anvil buttress is secured to tissue and separated from the anvil body upon a firing of the end effector; and
   a cartridge assembly having a cartridge body that supports a cartridge buttress, the cartridge buttress includes a second distal alignment band having a proximal portion secured to a cartridge buttress body of the cartridge buttress, the second distal alignment band circumscribing a second elongated distal opening, the cartridge buttress secured to the cartridge body with a second structure so that besides the proximal portion of the second distal alignment band, the second distal alignment band is unattached from the end effector and extends distally from the cartridge buttress, the second elongated distal opening configured to simultaneously receive the cartridge body and a second cartridge buttress attached to the cartridge body through the second elongated distal opening when the cartridge buttress is secured to tissue and separated from the cartridge body upon the firing of the end effector.

2. The end effector of claim 1, wherein the first structure includes at least one suture.

3. The end effector of claim 2, wherein the at least one suture includes a distal suture, and wherein the anvil buttress includes distal suture recesses that receive the distal suture to facilitate securement of the distal portion of the anvil buttress body to the anvil body.

4. The end effector of claim 1, further comprising a proximal suture, and wherein the anvil buttress includes proximal suture recesses that receive the proximal suture to facilitate securement of a proximal portion of the anvil buttress to the anvil body.

5. The end effector of claim 4, wherein the proximal suture recesses define a proximal tail.

6. The end effector of claim 1, wherein the second structure includes at least one suture.

7. The end effector of claim 6, wherein the at least one suture includes a distal suture, and wherein the cartridge buttress includes distal suture recesses that receive the distal suture to facilitate securement of the distal portion of the cartridge buttress body to the cartridge body.

8. The end effector of claim 1, further comprising a proximal suture, and wherein the cartridge buttress includes proximal suture recesses that receive the proximal suture to facilitate securement of a proximal portion of the cartridge buttress to the cartridge body.

9. The end effector of claim 8, wherein the proximal suture recesses define a proximal tail.

10. The end effector of claim 1, wherein the cartridge body supports a removable staple cartridge.

11. The end effector of claim 1, wherein the anvil buttress is a first anvil buttress and the cartridge buttress is a first cartridge buttress, the first anvil and cartridge buttresses being part of a first buttress system, and wherein the end effector further includes a second buttress system including a second anvil buttress and a second cartridge buttress, wherein the second buttress system is configured to mount to the anvil and cartridge assemblies when the first buttress system is not mounted to the anvil and cartridge assemblies, wherein the first and second elongated distal openings of the first buttress system are configured to collectively receive the second buttress system, the anvil body, and the cartridge body therethrough to align the second buttress system relative to the first buttress system along a surgical line of tissue when the first buttress system is positioned along the surgical line of the tissue.

12. A surgical stapling apparatus, comprising:
    an elongated tubular body portion; and
    an end effector supported on the elongated tubular body portion, the end effector including:
       an anvil assembly having an anvil body that supports an anvil buttress, the anvil buttress includes a distal alignment band that circumscribes a first elongated distal opening, the distal alignment band having a proximal portion with first and second ends secured to the anvil buttress and separated by the first elongated distal opening, the first distal alignment band defining at least one suture recess, the first elongated distal opening being configured to simultaneously receive the anvil body and a second anvil buttress attached to the anvil body through the first elongated distal opening when the anvil buttress is secured to tissue and separated from the anvil body upon a firing of the end effector;
       at least one suture received within the at least one suture recess to secure a distal portion of the anvil buttress to the anvil body so that the first distal alignment band and at least a majority of the first elongated distal opening extend distally beyond the anvil assembly and are unattached to the end effector other than by the proximal portion of the distal alignment band; and
       a cartridge assembly having a cartridge body that supports a cartridge buttress, the cartridge buttress includes a distal alignment band that extends distally beyond the cartridge body.

13. The surgical stapling apparatus of claim 11, wherein the at least one suture includes a proximal suture, and wherein the anvil buttress includes proximal suture recesses that receive the proximal suture to facilitate securement of a proximal portion of the anvil buttress to the anvil body.

14. The surgical stapling apparatus of claim 13, wherein the at least one suture includes a distal suture, and wherein the at least one suture recess includes distal suture recesses that receive the distal suture to facilitate securement of a distal portion of the anvil buttress to the anvil body.

15. The surgical stapling apparatus of claim 13, wherein the proximal suture recesses define a proximal tail.

16. The surgical stapling apparatus of claim 12, wherein the cartridge buttress is secured to the cartridge body by at least one suture.

17. The surgical stapling apparatus of claim 12, further comprising a proximal suture, and wherein the cartridge buttress includes proximal suture recesses that receive the proximal suture to facilitate securement of a proximal portion of the cartridge buttress to the cartridge body.

18. The surgical stapling apparatus of claim 17, further comprising a distal suture, and wherein the cartridge buttress includes distal suture recesses that receive the distal suture to facilitate securement of a distal portion of the cartridge buttress to the cartridge body.

19. The surgical stapling apparatus of claim 17, wherein the proximal suture recesses define a proximal tail.

20. The surgical stapling apparatus of claim 12, wherein the cartridge body supports a removable staple cartridge.

* * * * *